(12) United States Patent
Marashdeh et al.

(10) Patent No.: US 10,746,685 B2
(45) Date of Patent: Aug. 18, 2020

(54) MULTI-DIMENSIONAL APPROACH TO IMAGING, MONITORING, OR MEASURING SYSTEMS AND PROCESSES UTILIZING CAPACITANCE SENSORS

(71) Applicant: Tech4Imaging LLC, Columbus, OH (US)

(72) Inventors: Qussai Marashdeh, Columbus, OH (US); Benjamin Straiton, Pataskala, OH (US); Christopher Zuccarelli, Columbus, OH (US)

(73) Assignee: Tech4Imaging LLC, Columbus, OH (US)

( * ) Notice: Subject to any disclaimer, the term of this patent is extended or adjusted under 35 U.S.C. 154(b) by 0 days.

(21) Appl. No.: 16/449,934

(22) Filed: Jun. 24, 2019

(65) Prior Publication Data

US 2019/0310217 A1    Oct. 10, 2019

Related U.S. Application Data

(63) Continuation of application No. 15/610,091, filed on May 31, 2017.

(51) Int. Cl.
  *G01N 27/22* (2006.01)
  *G01F 1/64* (2006.01)
  (Continued)

(52) U.S. Cl.
  CPC ............ *G01N 27/226* (2013.01); *A61B 5/05* (2013.01); *G01F 1/64* (2013.01); *G01N 27/228* (2013.01); *G06T 11/003* (2013.01)

(58) Field of Classification Search
  CPC ............ A61B 5/05; G01F 1/64; G01N 27/228
  See application file for complete search history.

(56) References Cited

U.S. PATENT DOCUMENTS

| 5,130,661 A | 7/1992 | Beck et al. |
| 5,262,730 A | 11/1993 | Smith et al. |

(Continued)

FOREIGN PATENT DOCUMENTS

| CN | 102954854 A | 3/2013 |
| EP | 0606115 A1 | 7/1994 |

(Continued)

OTHER PUBLICATIONS

Abdilla, L. et al., Eddy Current Sensing Using Planar Coils, IEEE Instrumentation & Measurement Magazine, Dec. 2012.

(Continued)

*Primary Examiner* — Alvaro E Fortich
(74) *Attorney, Agent, or Firm* — Standley Law Group LLP

(57) ABSTRACT

A system and method for imaging, monitoring, or measuring systems and processes utilizing only data provided from capacitance sensors. The present invention combines the multi-frequency method of both ECVT/AECVT and DCPT to image or measure processes and systems more efficiently and accurately than the methods alone. The present system analyzes capacitance and current phase acquired at multiple frequencies to determine a plurality of properties of single and multiphase systems all at once. The combined use of ECVT and DCPT in multiphase flow can also be extended to measure volume fraction and phase distribution of flows involving greater than three phases by using multiple frequencies for capacitance, current phase, or both.

33 Claims, 12 Drawing Sheets

(51) Int. Cl.
*G06T 11/00* (2006.01)
*A61B 5/05* (2006.01)

(56) References Cited

U.S. PATENT DOCUMENTS

| | | | |
|---|---|---|---|
| 5,279,163 | A | 1/1994 | D'Antonio et al. |
| 6,208,204 | B1 | 3/2001 | Suzuki et al. |
| 7,424,462 | B2 | 9/2008 | Avni et al. |
| 7,684,846 | B2 | 3/2010 | Johnson et al. |
| 8,461,852 | B2 | 6/2013 | Yang et al. |
| 8,508,238 | B2 | 8/2013 | Mahalingam et al. |
| 8,519,722 | B1 | 8/2013 | Prendergast |
| 8,614,707 | B2 | 12/2013 | Warsito et al. |
| 8,867,928 | B2 | 10/2014 | Piehler |
| 9,016,143 | B2 | 4/2015 | Mamigonians |
| 9,170,224 | B2 | 10/2015 | Fan et al. |
| 9,259,168 | B2 | 2/2016 | Marashdeh et al. |
| 9,579,038 | B2 | 2/2017 | Brunner et al. |
| 9,581,560 | B2 | 2/2017 | Fan et al. |
| 9,927,385 | B2 | 3/2018 | Marashdeh et al. |
| 2002/0028010 | A1 | 3/2002 | Toida |
| 2003/0020493 | A1* | 1/2003 | Haase ............ G01F 1/712 324/664 |
| 2003/0173958 | A1 | 9/2003 | Goldfine et al. |
| 2004/0233191 | A1 | 11/2004 | Mukherjee et al. |
| 2005/0167588 | A1 | 8/2005 | Donnangelo |
| 2007/0024278 | A1 | 2/2007 | Walters et al. |
| 2007/0133746 | A1 | 6/2007 | Ortiz Aleman et al. |
| 2008/0116995 | A1 | 5/2008 | Kim et al. |
| 2009/0272028 | A1 | 11/2009 | Drozd et al. |
| 2010/0132473 | A1 | 6/2010 | Willcox |
| 2010/0148804 | A1 | 6/2010 | Jakoby et al. |
| 2010/0198638 | A1* | 8/2010 | Deffenbaugh ......... G06Q 10/30 705/308 |
| 2010/0332170 | A1 | 12/2010 | Gao et al. |
| 2011/0109911 | A1 | 5/2011 | Podoleanu |
| 2012/0182546 | A1* | 7/2012 | Chaouki ............ G01N 21/3563 356/73 |
| 2012/0268135 | A1 | 10/2012 | Marsala et al. |
| 2013/0144548 | A1 | 6/2013 | Xie |
| 2013/0187641 | A1 | 7/2013 | Singer |
| 2013/0275082 | A1 | 10/2013 | Follmer et al. |
| 2013/0327154 | A1 | 12/2013 | Xie et al. |
| 2014/0331783 | A1 | 11/2014 | Xie |
| 2014/0361793 | A1 | 12/2014 | Marashdeh et al. |
| 2014/0365009 | A1 | 12/2014 | Wettels |
| 2014/0365152 | A1 | 12/2014 | Marashdeh et al. |
| 2015/0048852 | A1 | 2/2015 | Marashdeh et al. |
| 2015/0338364 | A1 | 11/2015 | Fan et al. |
| 2016/0025663 | A1 | 1/2016 | Lehikoinen et al. |
| 2016/0076926 | A1 | 3/2016 | McCann et al. |
| 2016/0091448 | A1 | 3/2016 | Soleimani |
| 2016/0206227 | A1 | 7/2016 | Marashdeh et al. |
| 2016/0310040 | A1 | 10/2016 | Marashdeh |
| 2016/0327503 | A1 | 11/2016 | Marashdeh et al. |
| 2017/0241817 | A1 | 8/2017 | Marashdeh et al. |
| 2017/0261357 | A1 | 9/2017 | Wang et al. |

FOREIGN PATENT DOCUMENTS

| | | |
|---|---|---|
| WO | 2010007096 A3 | 1/2010 |
| WO | 2011002793 A1 | 1/2011 |
| WO | 2015142610 A1 | 9/2015 |
| WO | 2016078665 A1 | 5/2016 |

OTHER PUBLICATIONS

Ahmad, I. et al., Comparisons of Sensor Position for Electrical Capacitance Volume Tomography (Ecvt), Modern Applied Science, 2016, vol. 10, No. 4.

Hu, X. et al., An Impedance-Analyser-Based Multi-Channel Imaging System and Its Applications, IEEE International Workshop on Imaging Systems and Techniques, Chania, Greece, Sep. 10-12, 2008.

Hu, X. et al., An Imaging System With Planar PCT-Coil Sensor Array, International Workshop on Imaging Systems and Techniques, Shenzhen, China, May 11-12, 2009.

Huang, S. et al., Development of a Portable Electrical Impedance Tomography Data Acquisition System for Near-Real-Time Spatial Sensing, SPIE Smart Structures and Materials + Nondestructive Evaluation and Health Monitoring, 2015, San Diego, California.

Mohan, S. et al., Simple Accurate Expressions for Planar Spiral Inductances, IEEE Journal of Solid-State Circuits, vol. 34, No. 10, Oct. 1999.

phys.org, Magnetic Atoms of Gold, Silver, and Copper Have Been Obtained, https://phys.org/news/2008-02-magnetic-atoms-gold-silver-copper.html.

Rahim, R. et al., PC Controlled Function Generator Using Direct Digital Synthesis (DDS) Technology for Electrical Capacitance Tomography, Jurnal Teknologi, 45, 2006.

Ren, Z., Exploration of Medical Applications of Electrical Capacitance Tomography, Thesis submitted to The University of Manchester 2015.

Chew, W. et al., Reconstruction of Two-Dimensional Permittivity Distribution Using the Distorted Born Iterative Method, IEEE Transactions on Medical Imaging, Jun. 1990, pp. 218-225, vol. 9, No. 2.

Huang et al., Design of Sensor Electronics for Electrical Capacitance Tomography, IEE Proceedings G (Circuits, Devices and Systems), vol. 139, Issue 1, Feb. 1992, p. 83-88.

Marashdeh, Q. et al., Adaptive Electrical Capacitance Volume Tomography, IEEE Sensors Journal, Apr. 2014, pp. 1253-1259, vol. 14, No. 4.

Xie, C. et al., Electrical Capacitance Tomography for Flow Imaging: System Model for Development of Image Reconstruction Algorithms and Design of Primary Sensors, IEEE Proceedings-G, Feb. 1992, pp. 89-98, vol. 139, No. 1.

Yang, W. et al., Image Reconstruction Algorithms for Electrical Capacitance Tomography, Measurement Science and Technology 14, 2003, pp. R1-R13.

Marashdeh, et al., "On the ECT Sensor Based Dual Imaging Modality System for Electrical Permittivity and Conductivity Measurements", 2006, pp. 1-6, The Ohio State University, Columbus, Ohio.

Warsito, et al., "Electrical Capacitance Volume Tomography", 2007, pp. 1-9.

Covilakam, M., "Evaluation of Structural Monitoring Methods for Large Diameter Water Transmission Pipelines", Dec. 2011, The University of Texas at Arlington.

Wang,F. et al., Electrical Capacitance Volume Tomography: Design and Applications, Sensors, 2010 pp. 1890-1917.

Wikipedia, Electrical Capacitance Volume Tomography, https://en.wikipedia.org/w/index.php?title=Electrical_capacitance_volume_tomography&oldid=868112998, site visited Dec. 7, 2018.

Gunes, C. et al., A Comparison Between Electrical Capacitance Tomography and Displacement-Current Phase Tomography, IEEE Sensors Journal, Dec. 15, 2017, vol. 17, No. 24.

Wegleiter, H. et al., Development of a Displacement Current-Based Sensor for Electrical Capacitance Tomography Applications, Flow Measurement and Instrumentation, 2008, pp. 241-250.

* cited by examiner

Signal Flow

Typical ECVT Sensor

Flexible Sensor Top View

Flexible Sensor

1x3 Axial Meta Plate

3x3 Axial Meta Plate

Adaptive Sensor

Stages of the Multi-Dimensional Approach

Stages of the Multi-Dimensional Approach With Feedback

Stage 1 of the Multi-Dimensional Approach

Stage 3 of the Multi-Dimensional Approach

Stage 2 of the Multi-Dimensional Approach

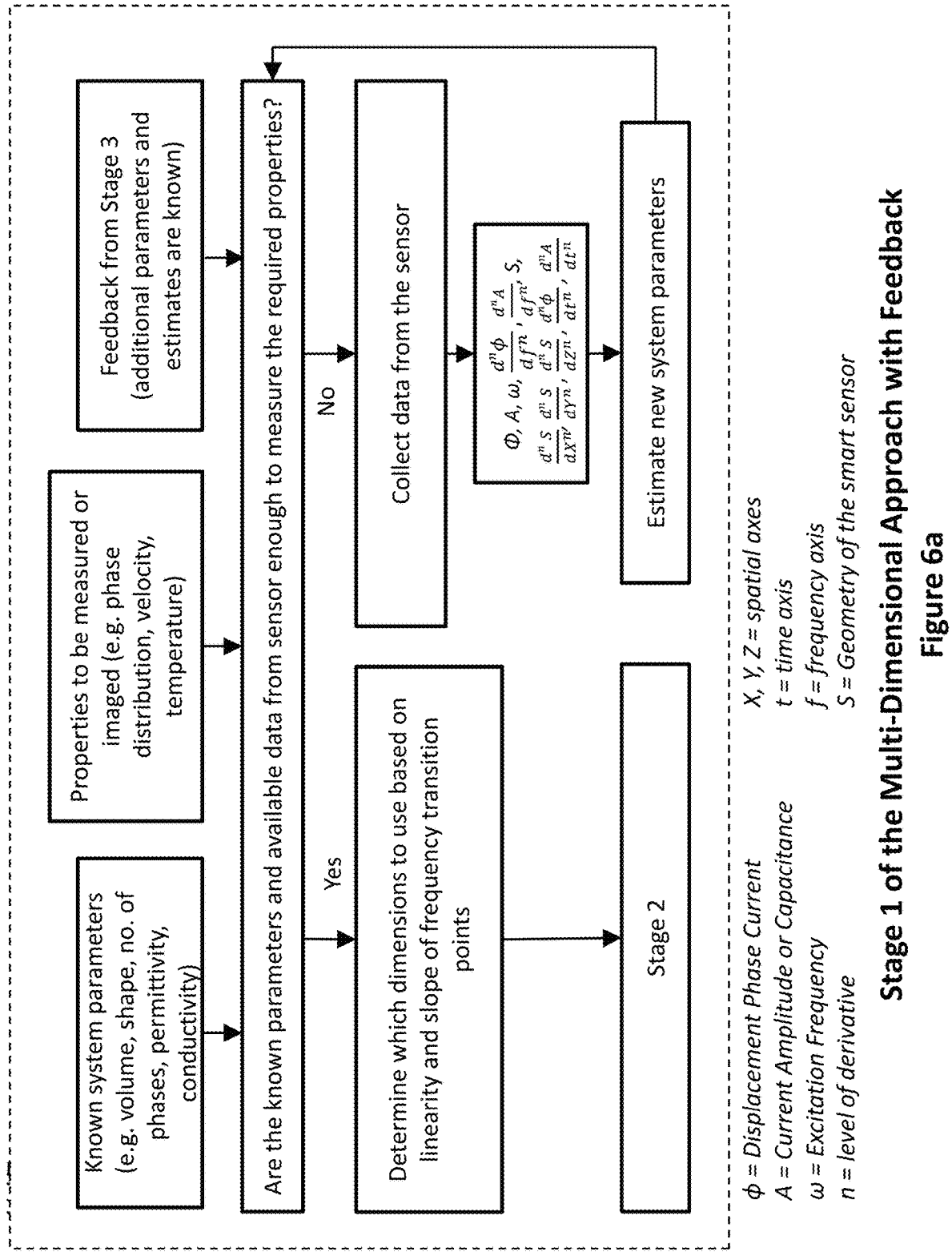

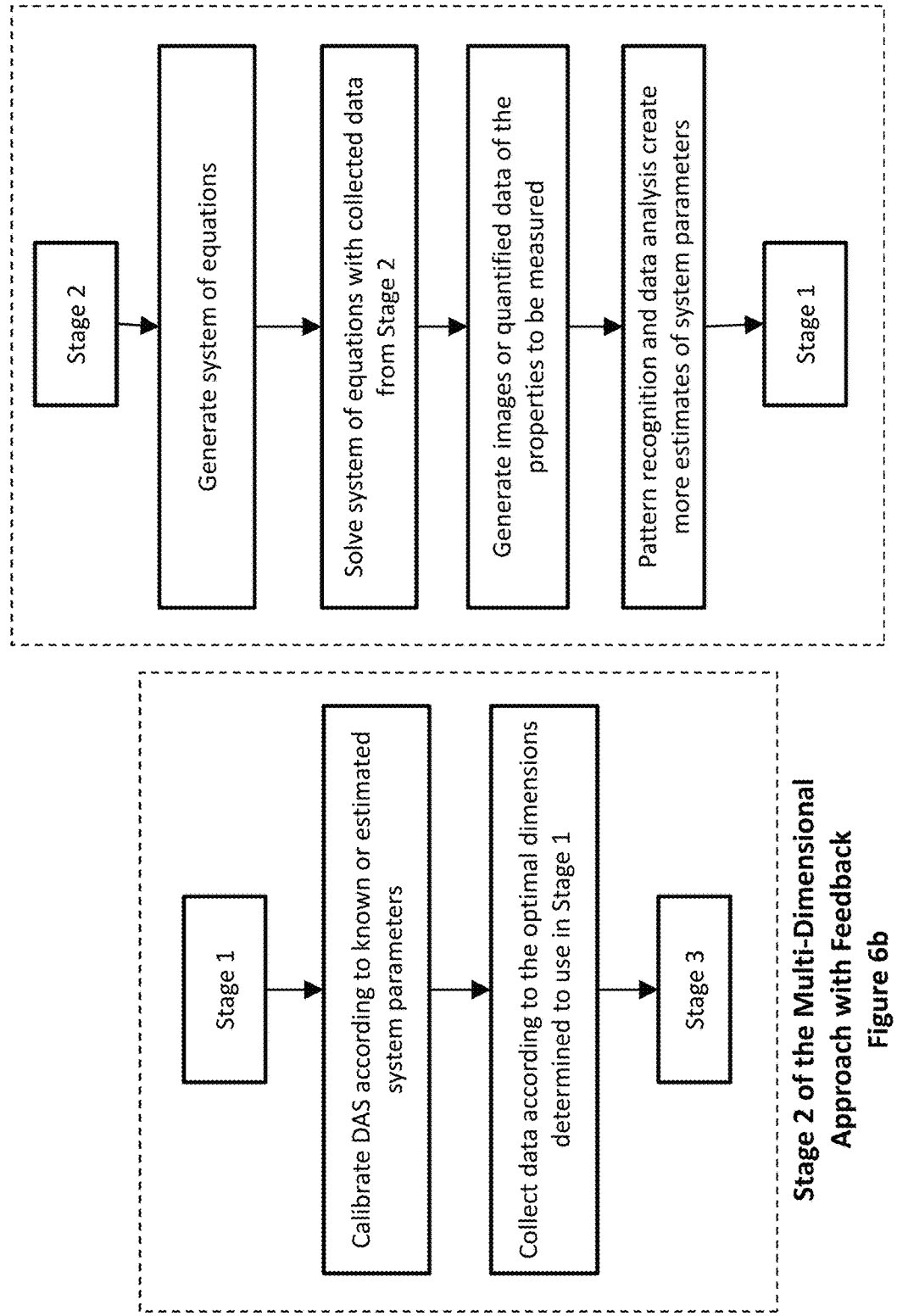

Embodiment of Estimating New System Parameters – Form Smart Sensor Geometry

Embodiment of Estimating New System Parameters – Detect Smart Sensor Geometry

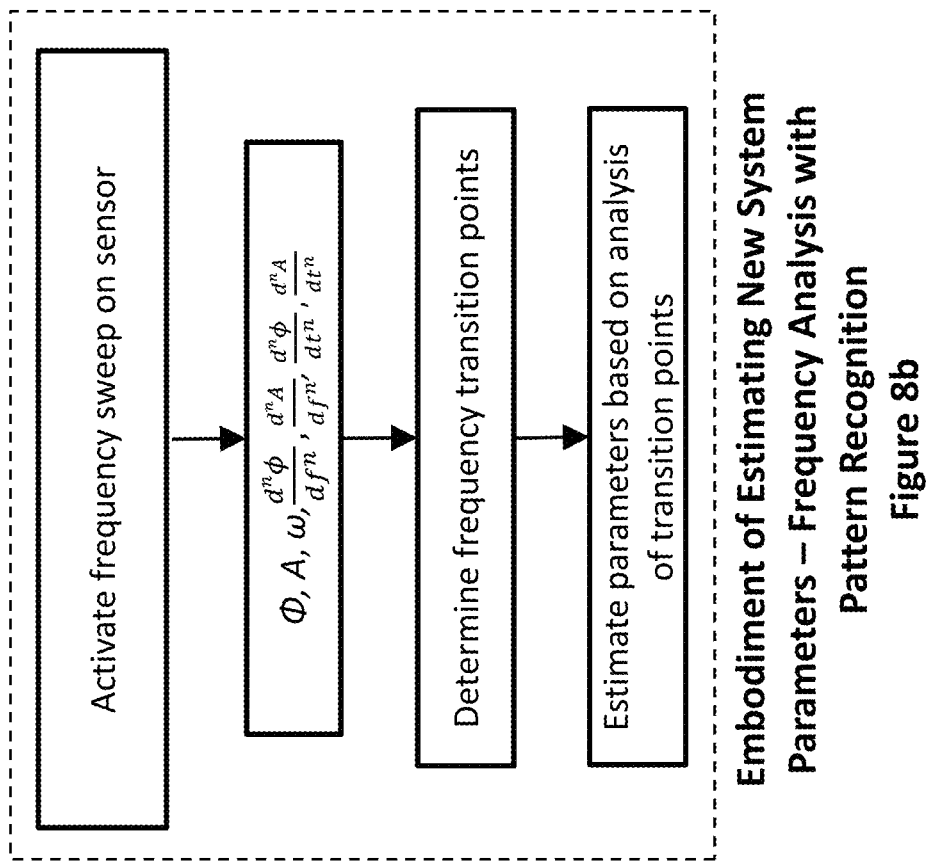
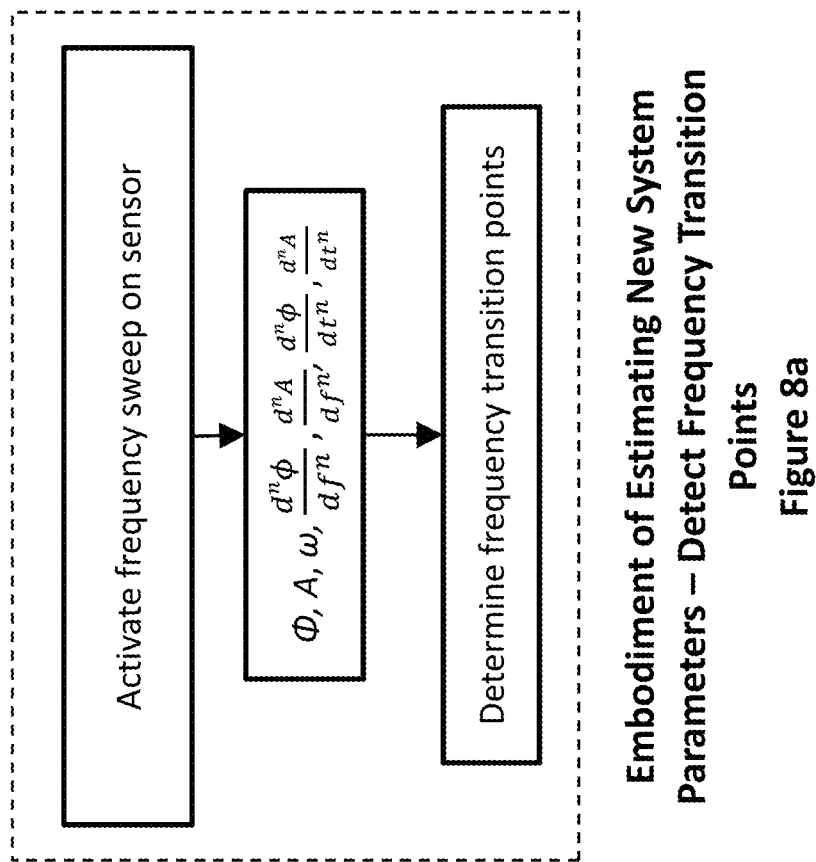

Embodiment of Estimating New System Parameters – AECVT Co-Design

Basic circuit building block for measuring receiver signal amplitude and phase at different frequencies

MULTI-DIMENSIONAL APPROACH TO IMAGING, MONITORING, OR MEASURING SYSTEMS AND PROCESSES UTILIZING CAPACITANCE SENSORS

CROSS-REFERENCE TO RELATED APPLICATIONS

This application is a continuation of U.S. application Ser. No. 15/610,091, filed Sep. May 31, 2017, the content of which is incorporated by reference as if fully recited herein.

BACKGROUND AND SUMMARY OF THE INVENTIVE FIELD

Electrical Capacitance Tomography (ECT) is the cross-sectional image reconstruction of the concentration of materials in the imaging domain by inverting capacitance data obtained from a capacitance sensor. Electrical Capacitance Volume Tomography (ECVT) is the non-invasive volumetric image reconstruction of materials in the imaging domain utilizing 3D features in the capacitance sensor design. An ECVT system is generally comprised of a sensor, data acquisition system, computer system and software for reconstruction of the 3D image representing the volume inspected by the sensor. An ECVT sensor is generally comprised of a plurality (n) of electrodes or plates placed around or near a region of interest, which, in one embodiment, provides n(n−1)/2 independent capacitance measurements which are used for image reconstruction. Capacitance data collected from the electrodes or plates placed around or near the region of interest are used to achieve the image reconstruction. ECVT technology is described in U.S. Pat. No. 8,614,707 to Warsito et al. which is hereby incorporated by reference.

ECVT applications span a wide array of industries. ECVT has been most recently applicable to multiphase flow applications commonly employed in many industrial processes, but may also be applied to single phase and stationary applications that require non-invasive imaging, measuring, or monitoring. In ECVT, sensor plates are distributed around the circumference or along the edge of a column, object, volume, or vessel under interrogation. The number of sensor plates used to acquire data can be increased to acquire more capacitance data. However, if there is a fixed surface area that the sensor plates may occupy, increasing the number of sensor plates reduces the area of each sensor plate accordingly. There is a limit for the minimum area of a sensor plate for a given object diameter or length, thus limiting the maximum number of plates that can be used in an ECVT sensor. This limit is determined through the required signal to noise ratio of the data acquisition system since the capacitance level of a sensor plate pair is directly proportional to the size of the plate. Furthermore, a minimum capacitance level is required to sense the changes in the sensing region. The limitation on the smallest size of the sensor plates, when increasing the number of sensor plates in an ECVT sensor, is one of the major hurdles in obtaining a high resolution imaging system through ECVT.

In pursuit of overcoming this challenge, the invention of Adaptive Electrical Capacitance Volume Tomography (AECVT) was created, in which the number of independent capacitance measurements can be increased through the use of modifiable meta-sensor plates comprised of many smaller sensor plates. These meta-sensor plates preserve the minimum area for a given signal-to-noise ratio and while also allowing for multiple configurations of meta-sensor plates in creating larger sensor plate pairs.

Adaptive Electrical Capacitance Volume Tomography (AECVT) provides higher resolution volume imaging of capacitance sensors based on different levels of activation levels on sensor plate segments. In AECVT systems, electrodes are comprised of an array of smaller capacitance segments that may be individually addressed. For example, each segment may be activated with different amplitudes, phase shifts, or frequency to provide the desired sensitivity matrix distribution. The sensor electronics of the present invention is designed to detect and measure the capacitance for the adaptive ECVT sensor of the present invention. For example, the difference in electrical energy stored in the adaptive ECVT sensor would be measured between an empty state and a state where an object is introduced into the imaging domain (e.g., between the electrodes). In a preferred embodiment of the invention, the term "adaptive" means the ability to provide selective or high resolution control through the application of voltage or voltage distributions to a plate having an array of capacitance segments. The change in overall energy of the system due to the introduction of a dielectric material in the imaging domain is used to calculate the change in capacitance related to the dielectric material. The change in capacitance can be calculated from the change in stored energy. Sensor electronics can also be designed by placing individual segment circuits in parallel yielding a summation of currents representing total capacitance between segments under interrogation. By individually addressing the capacitance segments of the electrodes of the present invention, electric field distribution inside the imaging domain can be controlled to provide the desired sensitivity matrix, focus the electric field, and increase overall resolution of reconstructed images. Voltage distribution can also be achieved by using a conventional measuring circuit with a sensor that distributes voltages through a voltage divider.

In AECVT systems, a capacitance measurement circuit is connected to electrodes (detecting or receiving electrode) of the adaptive sensor so that a capacitance measurement can be obtained for the selected source and detecting electrodes. The capacitors Cx1-Cxn of the sensor represent the n number of capacitance segments of the selected source electrode and the detecting electrode. Each capacitance segment of the electrodes can be individually addressed by separated voltage sources. These voltage sources are used for regulating the voltage levels and phase shifts on the capacitance segments of each of the electrodes on the adaptive sensor. The voltage across each of the capacitor segments (Vxn) is the combination of the voltage source Vi and the voltage sources connected to each capacitor segment (Vn). Accordingly, the measured Vo can be used to calculate each of the equivalent capacitance (Cxn) of the capacitance segments of the activated electrode. The associated formula is for Cxn=Cx1=Cx2. . . =Cxi. For segments with different capacitance values, the equivalent capacitance is calculated using the formula:

$$V_0 = \left(\frac{j\omega R_f}{1+j\omega C_f R_f}\right)\left(\sum_{i=1}^{n} V_{xi} C_{xi}\right)$$

As discussed, in one embodiment, n(n−1)/2 independent mutual capacitance measurements are measured and used for image reconstruction. For example, the capacitance between each of the electrodes of the sensor are measured in turn and image reconstruction is performed using this capacitance data. In other words, capacitance measurements are obtained from every pair or electrode combination of the sensor, in turn, to be used in image reconstruction. It is appreciated that the voltage sources herein discussed may be connected to the capacitance segments of each of the electrodes of the sensor array using known switch technologies. Using switches, the system can selectively choose which electrodes to activate by connecting the voltage sources to the selected electrodes through the switches. In another embodiment, switching or multiplexing circuit elements can be used to connect the appropriate voltage sources to each of the capacitance segments of the selected electrode allowing various elements to be selectively connected to each capacitance segment depending on the focus and sensitivity desired. For example, voltage sources of greater amplitude may be switched or connected to the capacitance segments in the center of the electrode or imaging domain so as to focus the measurements towards the center of the electrode or imaging domain.

In an alternate embodiment, instead of using different amplitudes, different frequencies may be used to activate electrode segments enabling concurrent measurements of different capacitance values introduced by electric field beams of different frequencies. In yet another alternate embodiment, different phase shifts may be used to activate electrode segments enabling steering of the electric field inside the imaging domain. The measured change in output voltage can be used to calculate the change in capacitance levels between the capacitance segments which are then used to reconstruct volume images of objects or materials between the sensors. AECVT is described in U.S. Patent Application Publication US2013/0085365 A1 and U.S. Pat. No. 9,259,168 to Marashdeh et al. which are hereby incorporated by reference.

Non-linearity is often a problem in relating the material distribution and permittivity of the sensing region to the signal received by the capacitance sensor, especially in applications of higher permittivity materials such as water. This high permittivity, or dielectric constant, amplifies the non-linearity in the image reconstruction problem which can further complicate the process of extracting images and other information from the measured signal.

In pursuit of overcoming this challenge, the invention of Displacement Current Phase Tomography (DCPT) was created, in which the phase of the measured current from capacitance sensors is utilized to reconstruct the 3D image of the volume or object being inspected. Similar to ECVT, DCPT is a low-cost imaging technique with the potential of being very useful to image systems and processes where there is a high contrast in the dielectric constant between materials involved in the system or process or where the material being imaged is lossy due to presence of electric conductivity or dielectric loss.

In conventional ECVT, the current amplitude across the capacitor plates is measured, which is then used to calculate the mutual capacitance between a plate pair and then used to reconstruct a 3D image. When objects in the imaging domain are lossy (i.e., having electric conductivity or dielectric loss), there is additional information contained in the phase of the currents that can also be used for image reconstruction. The change in the current phase is nearly linear with the volume fraction for many lossy materials. In ECVT, the sensitivity map is based on the current phase information. The sensitivity map joins the capacitance (current amplitude) to the permittivity distribution, and thus the material distribution, in the imaging domain through a linear approximation. Because the current phase is also linearly related to material distribution, it can provide an alternative imaging process using a similar linearized sensitivity matrix. Comparable to conventional ECVT, the phase sensitivity matrix which is calculated for all pixel locations is used in conjunction with the measurement of the current phase to reconstruct the volumetric image of the material distribution (spatial distribution of the conductivity or dielectric loss) in the sensing region.

The phase information can also be used to deduce velocity of a material moving through the sensing region. There is a relaxation time, dependent on material conductivity and dielectric properties, between when the electric field is applied to a material and when the material fully responds in dielectric polarization. The material first enters the sensing region and is then polarized by the electric field. As the material exits the sensing region, the material is still polarized and relaxes according to its relaxation time constant. This relaxation occurring outside the sensor plate's effective zone produces a change in the phase of the measured current, and thus any changes in the measured displacement current phase of the sensor when material is through the sensing region can be directly related to the velocity of the material. This observation is useful when dealing with single phase flows where the effective capacitance does not change, which typically renders cross-correlation methods for calculating velocity useless under conventional ECVT methods. DCPT solves this ECVT problem by relating the measured current phase directly to the velocity of the moving material when the effective dielectric constant inside the sensing region does not change. DCPT technology is described in U.S. patent application Ser. No. 15/262,565 which is hereby incorporated by reference.

In multiphase systems, it may be necessary to acquire a full volumetric velocity profile (velocimetry) of the flow, or of each individual phase. Conventional techniques require cross-correlation of data, which is both computationally intense and error prone due to its dependency on image reconstruction. A novel technique exists for calculating the velocity profile of multiphase flows based on ECVT and AECVT capacitance sensors. Velocimetry technology is described in U.S. patent application Ser. No. 15/051,109 which is hereby incorporated by reference.

All of the ECVT, AECVT, and DCPT systems utilize data acquisition systems that improve imaging resolution through sensing capacitances and current phases from conventional 3D or adaptive capacitance sensors. Example, data acquisition systems are described in U.S. patent application Ser. No. 14/191,574 (Publication No. US-2014-0365152-A1) which is hereby incorporated by reference.

The measured capacitance and current phase are also a function of excitation frequency applied to the sender electrodes of the sensor. Changes in capacitance or current phase as a function of frequency can also be used to image multiple materials in the imaging domain similar to the Multi-Phase Flow Decomposition approach previously incorporated using ECVT technology. For example, as described in patent application Ser. No. 15/138,751, changes in effective dielectric constants at various frequencies have been used to image more than the conventional two materials in the imaging domain. In DCPT, changes in phase measurement at different frequencies can similarly be used to image more than two materials in the imaging domain.

This present invention relates to any process, approach, method, system, means, or technique that utilizes any combination of the dimensions herein disclosed to image, monitor, measure, classify or otherwise quantify a material, combination of materials, flow, process, or system. ECVT, AECVT, and DCPT are each referred to here as a "dimension". Specifically, a single dimension is comprised of a single one of the tomography techniques, ECVT, AECVT, or DCPT, or any derivative thereof with respect to time or space (such as in the case of velocimetry), and the data required to utilize the respective method of tomography (capacitance or current phase) collected at a single excitation frequency. This method of utilizing any combination of dimensions as described is called the Multi-Dimensional Approach using ECVT Sensors. As described in U.S. patent application Ser. No. 15/138,751 where the volume fractions and distributions of multiple phases in a multiphase flow can be determined using capacitance data collected at multiple frequencies from a capacitance sensor, and in U.S. patent application Ser. No. 15/262,565 (DCPT application) where the volume fractions and distributions of multiple lossy phases in a multiphase flow can be determined using current phase data collected at multiple frequencies from a capacitance sensor, this present invention combines the multi-frequency method of both ECVT/AECVT and DCPT to image or measure processes and systems more efficiently and accurately than either method alone.

In one embodiment, this present invention can be used to determine the volume fraction and phase distribution of phases involved in multi-phase flow. A multiphase flow is that which has multiple materials flowing. The volume fraction of each material (i.e., flow phase) is the volume that phase occupies out of the total volume imaged or measured by the sensor. The total volume fraction of all phases should add to 100% of the imaged or measured volume. Multi-phase flow systems are those systems with interactions between multiple materials each having distinct and homogenous physical properties. A "phase" in the context of materials (as opposed to signals), is a constituent in the flow that is separable and homogenous in its physical properties. In a multiphase flow system, certain phase physical properties are required to be measured or monitored in order to optimize or control the flow. Some of these physical properties may include phase concentration and distribution, velocity, and mass flow. Some applications require determining the volume fraction (e.g., 20% is sand), while other applications require imaging of the volume fraction distribution or phase distribution.

For example, in one embodiment of the invention:
1. the effective electric response of the material using capacitance sensors is measured using a multidimensional approach;
2. the effective electric response is a function of volume fraction distribution of mixed phases;
3. imaging using multidimensions tells us the volume fractions of each pixel;
4. if the phase distribution is desired, the volume fraction distribution of that phase alone is examined (note this step is direct from step 3, if one knows all volume fractions any of the volume fractions can be selected to study it's distribution) for each pixel. The collective volume fraction from all pixels of a phase gives us the phase distribution image;
5. the number of phases that the sensor can measure or image is a function of the number of dimensions in the measurements;
6. multidimensional approach uses several dimensions simultaneously to image more phases. The more dimensions available, the more phases that contribute to the total volume fraction that can be imaged.

The present invention can be used to measure volume fraction using the multidimensional approach regardless of whether the volume sensed is imaged. Some applications only require measurement of volume fraction without mapping it.

The relationship between effective dielectric constant, dielectric loss, and operating frequency is unique for each different combination of phase distribution and electrical properties. In this embodiment, each phase's electrical properties can be determined or measured, and it is the dynamic volume fraction distribution that is required to be determined in multiphase imaging. The effective capacitance and current phase reading from each plate pair in an ECVT system is dependent upon the nature of mixing of the multiple phases. For example, a system where all phases are in a homogeneous mixture has a different combined capacitance and phase reading than a system where phases are distinctly layered. This unique relationship allows the determination of phase distribution and volume fraction of three phase systems, where as traditional ECVT or DCPT alone can only determine phase distribution and volume fraction for two phase systems when utilizing only one frequency. Additionally, the electrical properties of the phases involved may create greater differences in capacitance and phase due to changes in volume fraction than in the case of capacitance or phase alone but across multiple frequencies for three phase systems, thus making determination of volume fraction and phase distribution more accurate and efficient with the combined ECVT/DCPT approach.

The combined use of ECVT and DCPT in multiphase flow can also be extended to measure volume fraction and phase distribution of flows involving greater than three phases by using multiple frequencies as already mentioned for capacitance, current phase, or both.

This present invention can be used to image, measure, monitor or otherwise quantify a wide array of properties of a moving or stationary—single or multiphase—system or process. The number of dimensions utilized in the multi-dimensional approach should be sufficient to generate a number of equations equal to or greater than the number of properties to be measured by the system. Examples of properties to be measured by the system include temperature, volume fraction, phase distribution, velocity, acceleration, mass flow rate, volumetric flow rate, viscosity, conductivity, charge or any property that can be related to a change in dielectric constant or dielectric loss in such possible applications as oil drilling and transportation, multi-phase reactors, fluidized beds, pneumatic conveying of solids, and medical imaging and monitoring.

The multi-dimensional approach is a dynamic process that is adaptable to a wide array of applications. In order to optimize the process, the correct dimensions should be chosen that best fit the application. In the preferred embodiment, the primary criterion for choosing the most appropriate dimensions is linearity. Given the required properties to be measured, the first decision is whether to use capacitance, current phase, a derivative of capacitance or current phase, or any combination of these to measure those properties. The decision is determined by the relationship between these properties to be measured and the dimension used to measure them. The dimension that retains the most linear relationship with the property to be measured under the conditions of the application is the one that is preferably applied. Once the optimal dimensions are identified for the application, the optimal frequency for each one is determined. If utilizing only one frequency, the frequency is chosen that yields the most linearity for the dimension with respect to the property to be measured. If using multiple frequencies, the determination is made using frequency transition points. Because dielectric constant and dielectric loss of a mixture can change as a function of frequency, these markers are located at frequencies where there are sharp transitions in dielectric constant or dielectric loss in the volume being sensed under the conditions of the application. These transition points will be most prevalent in multiphase systems or processes. By utilizing the Maxwell-Wagner-Sillars (MWS) polarization effect and the electrical properties of each individual phase, certain properties such as volume fraction of each phase can be measured.

Another method of identifying the frequency transition points involves running a sweep frequency signal of different frequency components and identifying frequency points where the effective dielectric constant or dielectric loss of a mixture undergoes a sharp transition. After the frequency points are identified, frequency markers are created. A frequency marker is an excitation signal composed of one frequency above and one frequency below the identified transition point. Additional markers can be designated for additional transition points. Each frequency marker measures the dimension (capacitance, current phase, or derivatives) at a frequency above and below its corresponding transition point. The difference in the measured dimension at different frequency markers is related to the property or distribution of the phase that caused this frequency transition phenomenon in the effective dielectric constant or dielectric loss. Because each phase has distinct electrical properties, the transition frequencies contributed by each phase is distinct in the frequency domain.

The process for measuring the desired properties of a system using the Multi-Dimensional Approach is comprised of (a) identifying which system parameters are known and unknown (e.g. number of phases, temperature, etc.) in a process or system; (b) identifying the properties of the system or process to be measured; (c) determining whether or not the known parameters are sufficient to measure the required properties with supplemental information from any combination of dimensions aforementioned; (d) gathering capacitance and current phase data across a range of frequencies and estimating required system parameters if the current known system parameters are insufficient to measure the required properties with supplemental information from any combination of dimensions aforementioned; (e) analyzing the dimensions, system parameters, and properties to be measured to determine which dimensions or combination of dimensions are most linearly related to the properties to be measured; (f) selecting those optimal dimensions; (g) employing those optimal dimensions to generate a system of equations equal to or greater in number than the number of properties to be measured; and (h) solving that system of equations to solve for and quantify the properties to be measured.

In one embodiment of the invention, the invention is comprised of: a sensor comprising a plurality of electrodes for placement near or around the vessel or the object, wherein the sensor is adapted to provide electric field distribution and sensor sensitivity in at least two geometric dimensions; a data acquisition circuit in communication with the sensor for receiving input data from the sensor, the input data including current output from the sensor and for outputting phase data for the current; a processing system in communication with the data acquisition circuit, the processing system programmed with instructions for executing on the processing system to convert detected capacitance data and phase data into an image or quantification of the volume being sensed.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 5a illustrates one embodiment of Stage 1 according to the linear configuration of the Multi-Dimensional Approach in FIG. 4a.

FIG. 5b illustrates one embodiment of Stage 2 according to the linear configuration of the Multi-Dimensional Approach in FIG. 4a.

FIG. 5c illustrates one embodiment of Stage 3 according to the linear configuration of the Multi-Dimensional Approach in FIG. 4a.

FIG. 6a illustrates one embodiment of Stage 1 according to the feedback configuration of the Multi-Dimensional Approach in FIG. 4b.

FIG. 6b illustrates one embodiment of Stage 2 according to the feedback configuration of the Multi-Dimensional Approach in FIG. 4b.

FIG. 6c illustrates one embodiment of Stage 3 according to the feedback configuration of the Multi-Dimensional Approach in FIG. 4b.

FIG. 8a illustrates one embodiment of estimating new system parameters as in FIG. 5a as frequency transition points can be detected by the system through a frequency sweep.

FIG. 8b illustrates one embodiment of estimating new system parameters as in FIG. 5a as pattern recognition may be used in conjunction with a frequency sweep to estimate additional system parameters.

DETAILED DESCRIPTION OF EXEMPLARY EMBODIMENT(S)

The following detailed description of the exemplary embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1B:
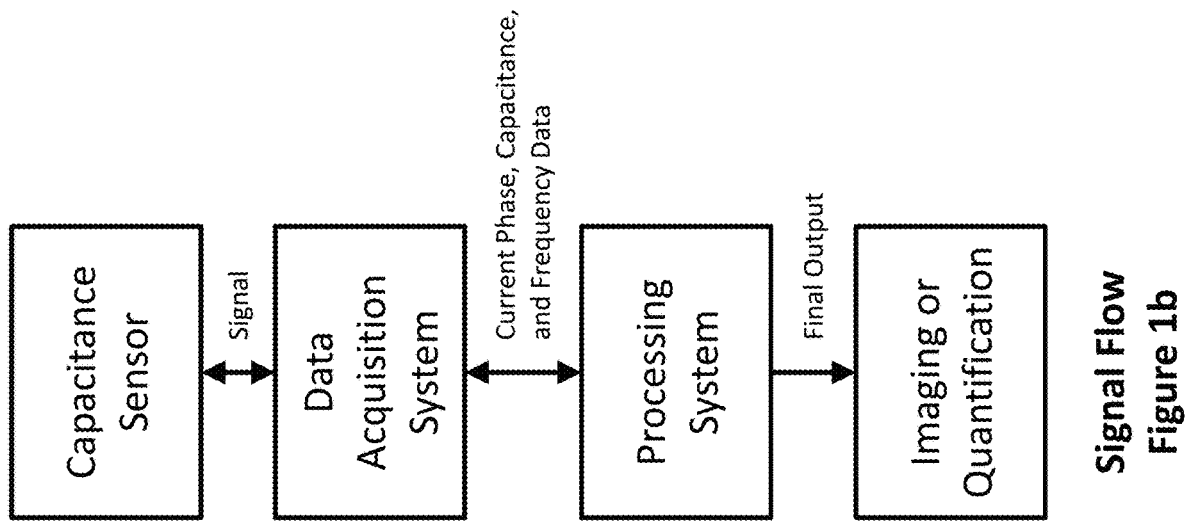
FIG. 1b illustrates the typical components and signal flow of the present invention.
Figure 1A:
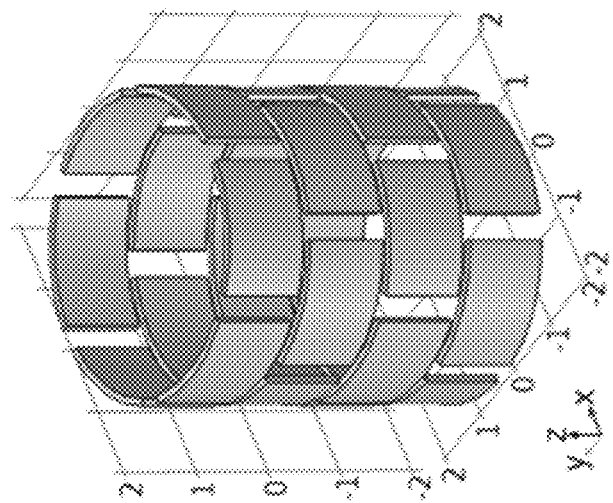
FIG. 1a illustrates a typical 24 electrode ECVT sensor with 4 layers of plates and exemplary measurements that the sensor may provide.

FIG. 1a illustrates a typical 24 electrode ECVT sensor with 4 planes of plates. It is appreciated that the sensor shape may be comprised of any size, shape, number, or orientation of plates. The sensor of the present invention may provide information on any of the listed parameters including signal phase, signal amplitude (capacitance), frequency response, or spatial geometry of the sensor. Additionally, any spatial derivative of the geometry (e.g., sensitivity matrix) may be obtained or any time or frequency derivative of signal phase or amplitude.

FIG. 1b illustrates the typical components and signal flow of the present invention, comprising: a capacitance sensor comprised of a plurality of electrodes which emit an alternating electrical field from an excite plate and detection of the resulting signal at a detect plate where the signal has been modified by the medium between the plates; a data acquisition system or measurement circuit which, in one embodiment, sends the excitation signal to the sensor excite plates, receives the signal from the detect plates, processes the received signal with a notch filter at the excitation frequencies, demodulates the signal to obtain amplitude and phase, and outputs the data to a processing system; a processing system which processes the data according to the Multi-Dimensional Approach and outputs the data as an image or other quantification. In an alternative embodiment, the activation circuit is separate from the measurement circuit.

Figure 2B:
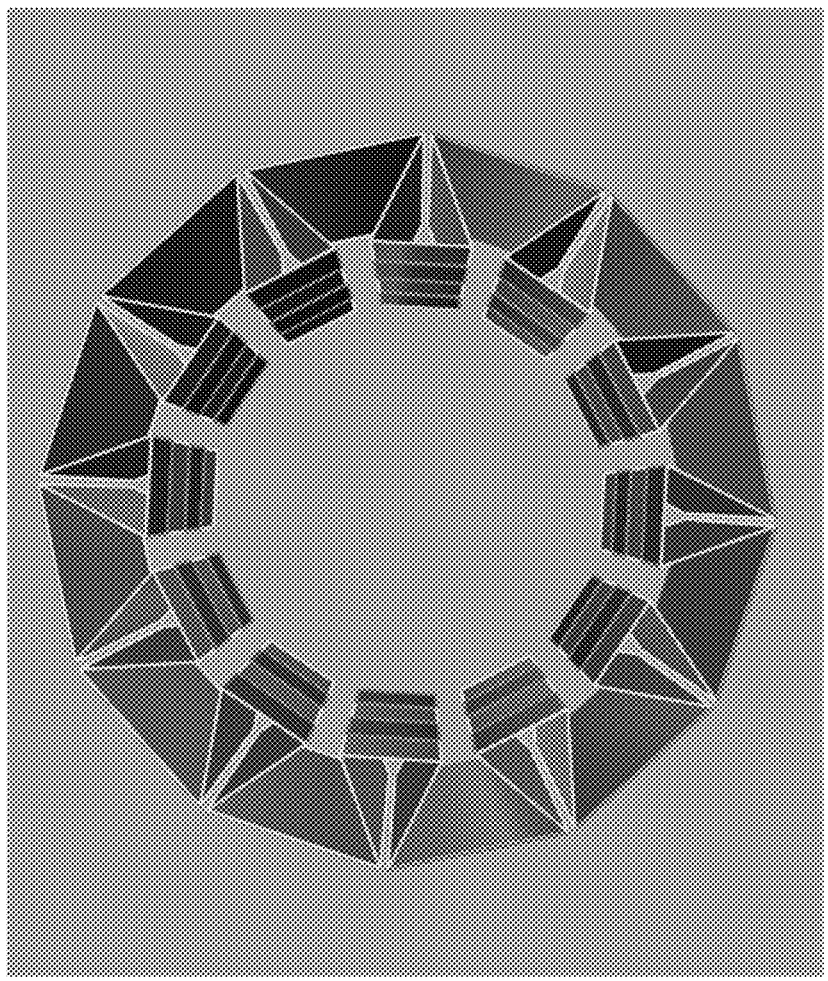
FIG. 2b illustrates the same sensor as in FIG. 2a from a top view of the sensor.
Figure 2A:
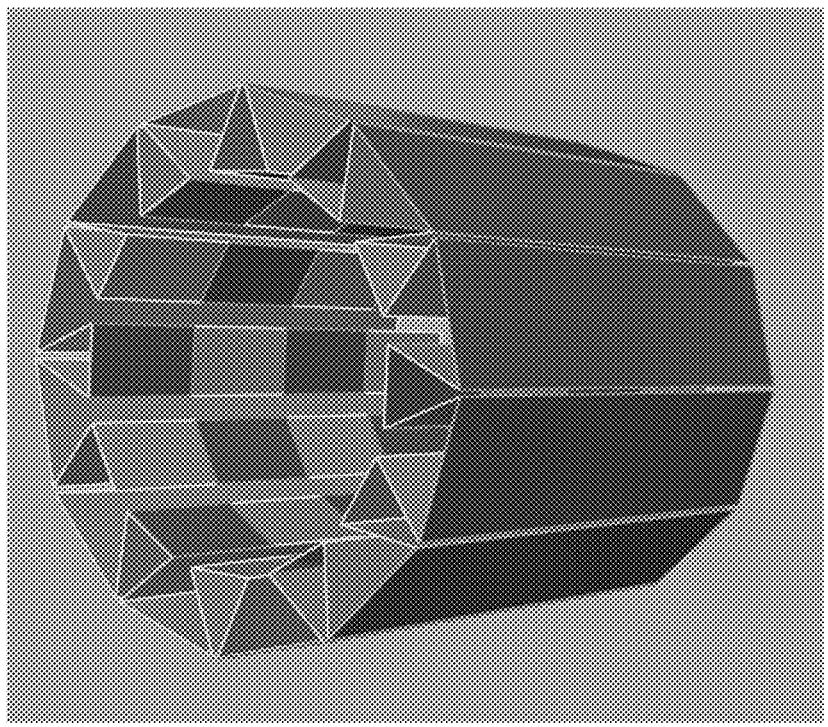
FIG. 2a illustrates a flexible ECVT sensor embodiment where the diameter of the sensor can change readily through mechanical means.

FIG. 2a illustrates one embodiment of the sensor for an ECVT system as a flexible sensor which may change diameter or other physical dimensions through mechanical means such as external compression and decompression forces or materials which respond to electrical or other stimuli. The conductive plates in the figure alternate with insulated space. The outer portions of this embodiment are conductive. FIG. 2b illustrates the flexible sensor embodiment in FIG. 2a from the top view of the sensor. This sensor is adapted to expand to fit around the object it is sensing.

Figure 3B:
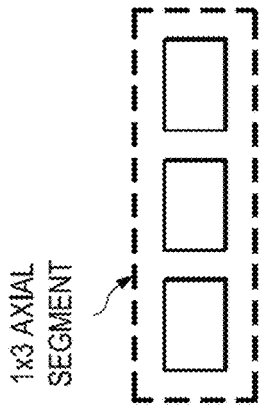
FIG. 3b illustrates a possible meta-plate configuration on an AECVT sensor utilizing 3 adjacent plates.
Figure 3C:
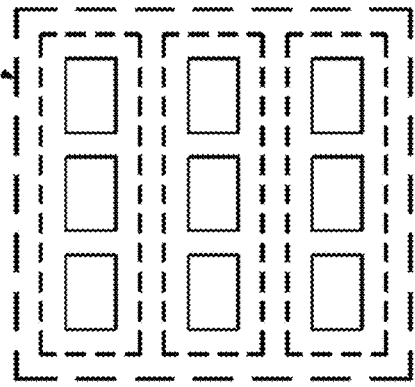
FIG. 3c illustrates a possible meta-plate configuration on an AECVT sensor utilizing 9 adjacent plates.
Figure 3A:
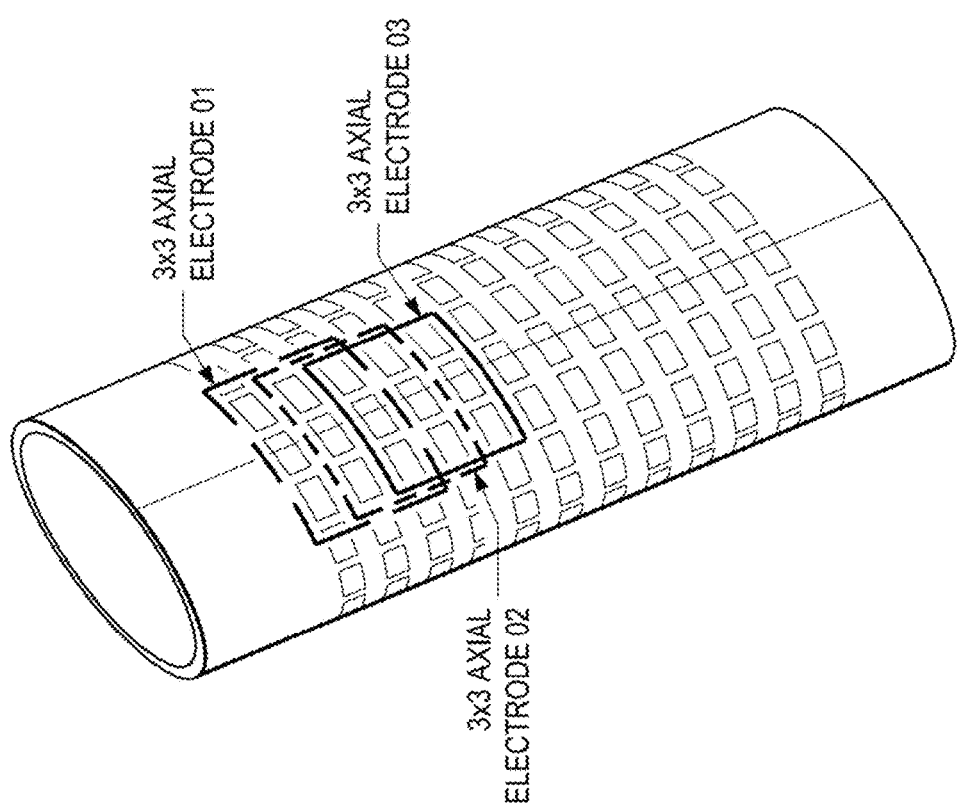
FIG. 3a illustrates an adaptive sensor embodiment for AECTV where the small electrode plates may be activated together to create a single larger meta-plate in far more numerous configurations than traditional ECVT.

FIG. 3a illustrates one embodiment of the sensor for an AECVT system as an adaptive sensor which may activate any group of smaller plates simultaneously to take measurements as one larger meta-plate. The configuration in which the meta-plates are formed can affect the measurements being taken and can be re-configured electrically to optimize the data being received from the sensor. The illustration depicts three overlapping meta-plate configurations, each with a small axial offset from the other (three electrodes 01, 02, 03 respectively). The overlapping shared space of each meta-plate allows a greater resolution of the interrogated space than traditional ECVT sensors. Additionally, different configurations of meta-plates may be used to optimize data collection for different applications such as in multiphase flow.

FIG. 3b illustrates an exemplary embodiment of a meta-plate by combining three adjacent plates in a 3×1 configuration. FIG. 3c illustrates an exemplary embodiment of a meta-plate by combining nine adjacent plates in a 3×3 configuration.

Figure 4A:
FIG. 4a illustrates the exemplary stages of the Multi-Dimensional Approach in a linear configuration.
Figure 4B:
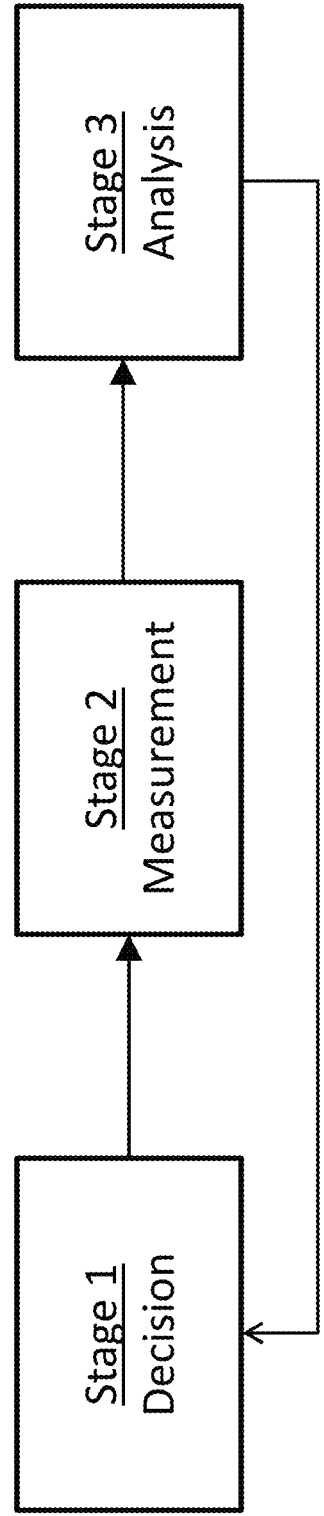
FIG. 4b illustrates the exemplary stages of the Multi-Dimensional Approach in a feedback configuration.

FIG. 4a illustrates an exemplary embodiment of the stages of the Multi-Dimensional approach as decision, measurement, and analysis, which are completed in a linear configuration. FIG. 4b illustrates an exemplary embodiment of the stages of the Multi-Dimensional Approach as decision, measurement, and analysis which are completed in a feedback configuration.

Figure 5A:
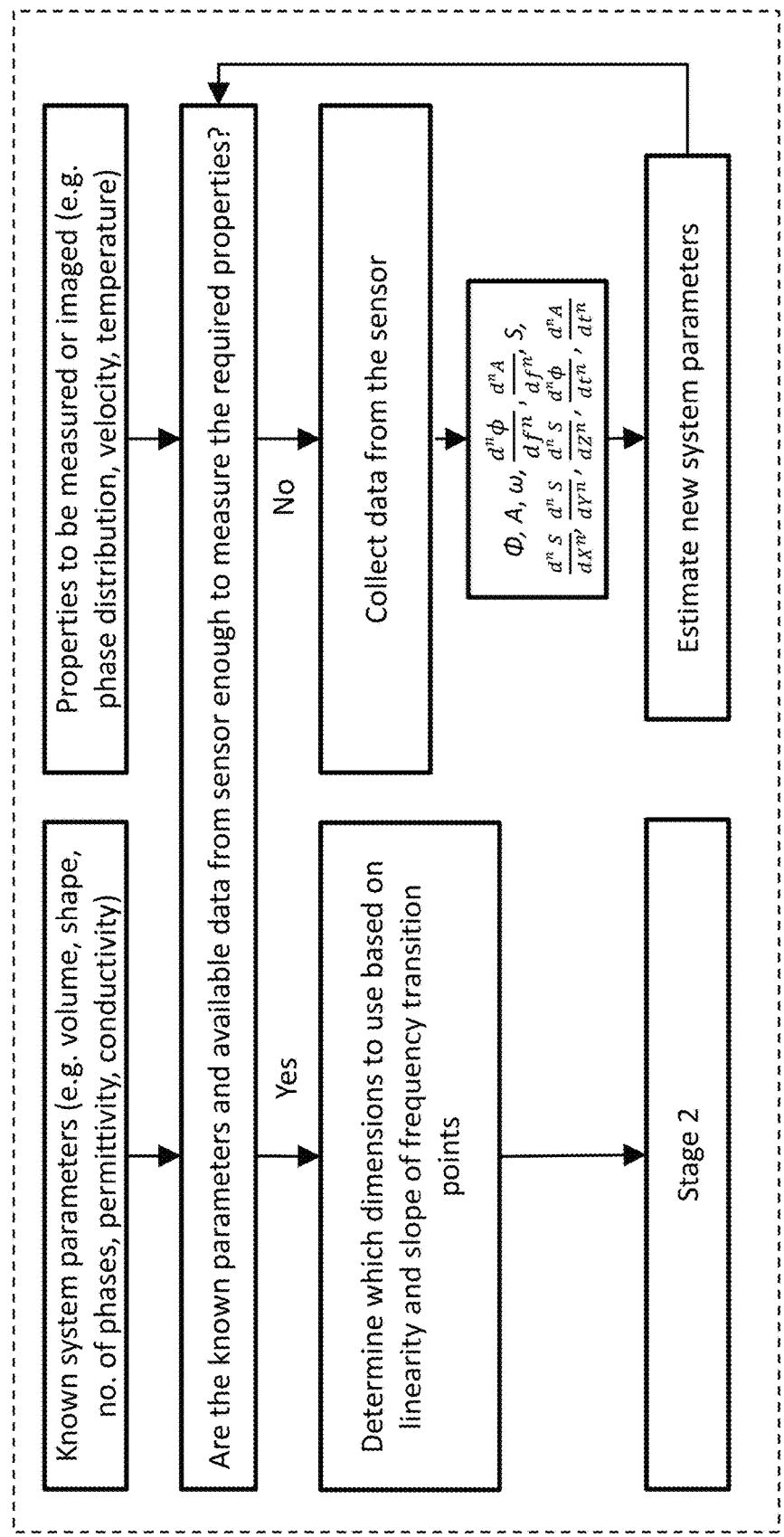

FIG. 5a illustrates an exemplary embodiment of the first stage as presented in FIG. 4a. This first stage is referred to as the decision stage. In this stage, a number of known system parameters are taken as input into the system along with the desired properties to be measured from the system (e.g., phase distribution, velocity, temperature). These inputs are used to determine the optimal configuration to collect data. The optimal configuration may include decisions about excitation frequency, phase manipulations, capacitance manipulations, or geometrical configuration of the sensor. If the given parameters are not enough to measure the required properties, then data may be collected from the sensor and used to estimate further system parameters which then make it possible to measure the required properties.

Figures 5B, 5C:
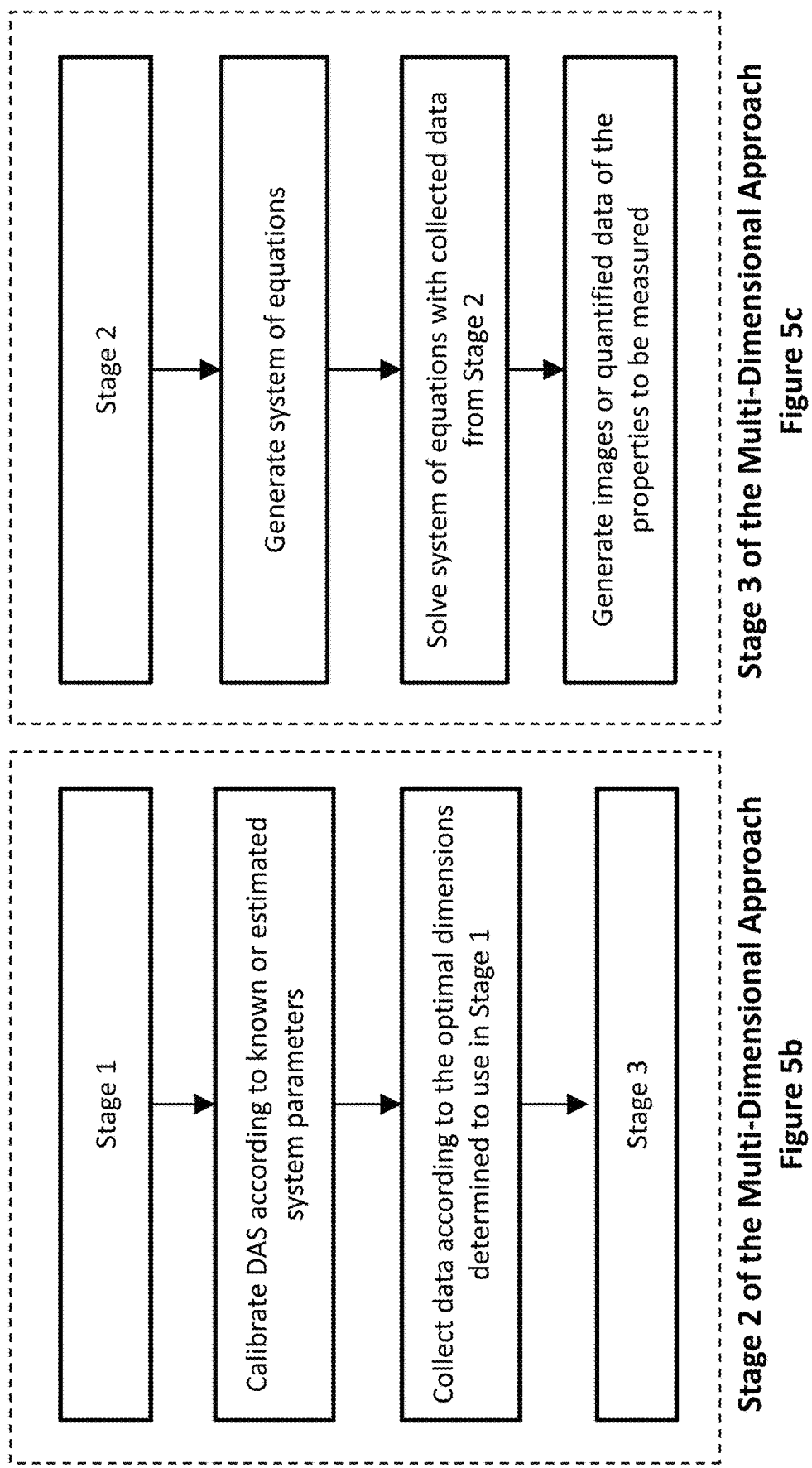

FIG. 5b illustrates an exemplary embodiment of the second stage as presented in FIG. 4a. This second stage is referred to as the measurement stage. In this stage, the optimal configuration is received from the first stage as input and the sensor and system are activated accordingly to collect data from the space to be interrogated.

FIG. 5c illustrates an exemplary embodiment of the third stage as presented in FIG. 4a. This third stage is referred to as the analysis stage. In this stage, the data from the second stage is taken as input to generate a system of equations which is solved with the collected data and the known/estimated parameters. Once the equations are solved, then the final output is the desired properties to be measured such as volume fraction, velocity, temperature, or multi-phase imaging. For example, see the following equations:

1—Volume Fraction

In the formulation below, four phases are considered to be measured in volume fraction, imaging, and velocimetry. The multidimensional approach allows for more equation to be formulated for solving more phases in the imaging domain. The example here is for illustration.

$$C_m^{M \times 1} = \epsilon_1^{M \times 1} \cdot S_{C1}^{M \times 1} + \epsilon_2^{M \times 1} \cdot S_{C2}^{M \times 1} + \epsilon_3^{M \times 1} \cdot S_{C3}^{M \times 1}$$

$$\phi_m^{M \times 1} = \epsilon_1^{M \times 1} \cdot S_{\phi 1}^{M \times 1} + \epsilon_2^{M \times 1} \cdot S_{\phi 2}^{M \times 1} + \epsilon_3^{M \times 1} \cdot S_{\phi 3}^{M \times 1}$$

$$\frac{\Delta C^{M \times 1}}{\Delta f_m} = \epsilon_1^{M \times 1} \cdot S_{\frac{\Delta C}{\Delta f}1}^{M \times 1} + \epsilon_2^{M \times 1} \cdot S_{\frac{\Delta C}{\Delta f}2}^{M \times 1} + \epsilon_3^{M \times 1} \cdot S_{\frac{\Delta C}{\Delta f}3}^{M \times 1}$$

$$\epsilon_1^{M \times 1} + \epsilon_2^{M \times 1} + \epsilon_3^{M \times 1} + \epsilon_4^{M \times 1} = \begin{matrix} 1 \\ \vdots \\ 1 \end{matrix}$$

Where $C_m^{M\times 1}$ is the measured capacitance vector, M is the number of capacitance data in the measured vector, $\in_1^{M\times 1}$, $\in_2^{M\times 1}$, $\in_3^{M\times 1}$, and $\in_4^{M\times 1}$ is the volume fraction of the phase 1, 2, 3 and 4 respectively. $S_{C1}^{M\times 1}$, $S_{C2}^{M\times 1}$, and $S_{C3}^{M\times 1}$ is the sensitivity of capacitance pairs to a change in volume fraction in phase 1, 2, and 3 respectively. $S_{\varnothing 1}^{M\times 1}$, $S_{\varnothing 2}^{M\times 1}$, and $S_{\varnothing 3}^{M\times 1}$ is the sensitivity of electric phase between plate pairs to a change in volume fraction in phases 1, 2, and 3 respectively $$S_{\frac{\Delta C}{\Delta f}1}^{M\times 1}, S_{\frac{\Delta C}{\Delta f}2}^{M\times 1}, \text{ and } S_{\frac{\Delta C}{\Delta f}3}^{M\times 1}$$

is the sensitivity of differential frequency response of capacitance between plate pairs to a change in volume fraction in phases 1, 2, and 3 respectively.

Without loss of generality, higher order derivative equations of capacitance or phase can be formulated to solve for more phases in the imaging domain. For example, second order derivative equations of the capacitance and phase for a four phase system can be formulated as:

$$\frac{\Delta^2 C^{M\times 1}}{\Delta^2 f_m} = \in_1^{M\times 1} \cdot S_{\frac{\Delta^2 C}{\Delta^2 f}1}^{M\times 1} + \in_2^{M\times 1} \cdot S_{\frac{\Delta^2 C}{\Delta^2 f}2}^{M\times 1} + \in_3^{M\times 1} \cdot S_{\frac{\Delta^2 C}{\Delta^2 f}3}^{M\times 1}$$

$$\frac{\Delta^2 \phi^{M\times 1}}{\Delta^2 f_m} = \in_1^{M\times 1} \cdot S_{\frac{\Delta^2 \phi}{\Delta^2 f}1}^{M\times 1} + \in_2^{M\times 1} \cdot S_{\frac{\Delta^2 \phi}{\Delta^2 f}2}^{M\times 1} + \in_3^{M\times 1} \cdot S_{\frac{\Delta^2 \phi}{\Delta^2 f}3}^{M\times 1}$$

2—Imaging Equations

For each phase in step 1 where the volume fraction vector has been calculated, imaging can be performed based on volume fraction step, for example, phase 1 capacitance equation, phase equation or differential frequency equation can be used to reconstruct an image of each phase. Below are examples of the capacitance, phase, and differential frequency equations through which the signal portion attributed to that phase is calculated.

$$C_1^{M\times 1} = \in_1^{M\times 1} \cdot S_{C1}^{M\times 1}$$

$$\phi_1^{M\times 1} = \in_1^{M\times 1} \cdot S_{\phi 1}^{M\times 1}$$

$$\frac{\Delta C^{M\times 1}}{\Delta f_1} = \in_1^{M\times 1} \cdot S_{\frac{\Delta C}{\Delta f}1}^{M\times 1}$$

To formulate an image based on one of those equations, one follows the typical reconstruction techniques developed and used in literature. For example, the Phase 1 can be reconstructed from the capacitance measurements following the equations below:

$$C_1^{M\times 1} = \in_1^{M\times 1} \cdot S_{C1}^{M\times 1} = S_{C1}^{M\times N} \in_1^{1\times N}$$

Following from the above, $$S_{C1}^{N\times M}(\in_1^{M\times 1} \cdot S_{C1}^{M\times 1}) = \in_1^{1\times N}$$

Where $S_{C1}^{M\times N}$ is the pixel wise sensitivity matrix, and $\in_1^{1\times N}$ is the image vector. On the other hand $S_{C1}^{M\times 1}$ is the volume fraction capacitance weight of phase 1 and $\in_1^{M\times 1}$ is the volume fraction vector of Phase 1.

From this point on, reconstruction algorithms can be used similar to ECVT or AECVT reconstruction.

3—Velocimetry:

From step 2, a velocimetry map can be calculated for each phase based on a selected dimension. For example, using capacitance related to phase 1 velocimetry equations for phase 1:

$$\dot{C} = g_{x1}v_{x1} + g_{y1}v_{y1} + g_{z1}v_{z1}$$

$$v_{x1} = g_{x1}^T \dot{C}_1$$

$$v_{y1} = g_{y1}^T \dot{C}_1$$

$$v_{z1} = g_{z1}^T \dot{C}_1$$

Where $\dot{C}_1$ denotes the time rate change of capacitance signal of phase 1. $v_{x1}$, $v_{y1}$, and $v_{z1}$ are the x, y, and z components of the velocity profile of phase 1, respectively. $g_{x1}$, $g_{y1}$, and $g_{z1}$ are the dot product between the image and the sensitivity gradient velocimetry for image vectors of the x, y, and z components of the velocity profile for phase 1.

FIG. 6a illustrates an exemplary embodiment of the first stage as presented in FIG. 4b. Similar to FIG. 5a, this figure depicts the flow of the decision stage with known parameters and properties to be measured as input. However, in addition to these inputs, this stage also takes feedback from stage 3 such as further determined system parameters to better refine the decision stage in optimizing data collection configurations.

FIG. 6b illustrates an exemplary embodiment of the second stage as presented in FIG. 4b. Similar to FIG. 5b, this figure depicts the flow of the measurement stage as taking the optimal configuration from stage 1 as input and collecting data accordingly.

FIG. 6c illustrates an exemplary embodiment of the third stage as presented in FIG. 4b. Similar to FIG. 5c, this figure depicts the flow of the analysis stage through generating and solving equations. However, in addition to the generation and solving of equations from data collected in stage 2, the flow here includes a step for pattern recognition and data analysis for the purposes of estimating additional parameters which can be fed back into stage 1 as input to optimize the data collection configuration even further.

Figures 7A, 7B:
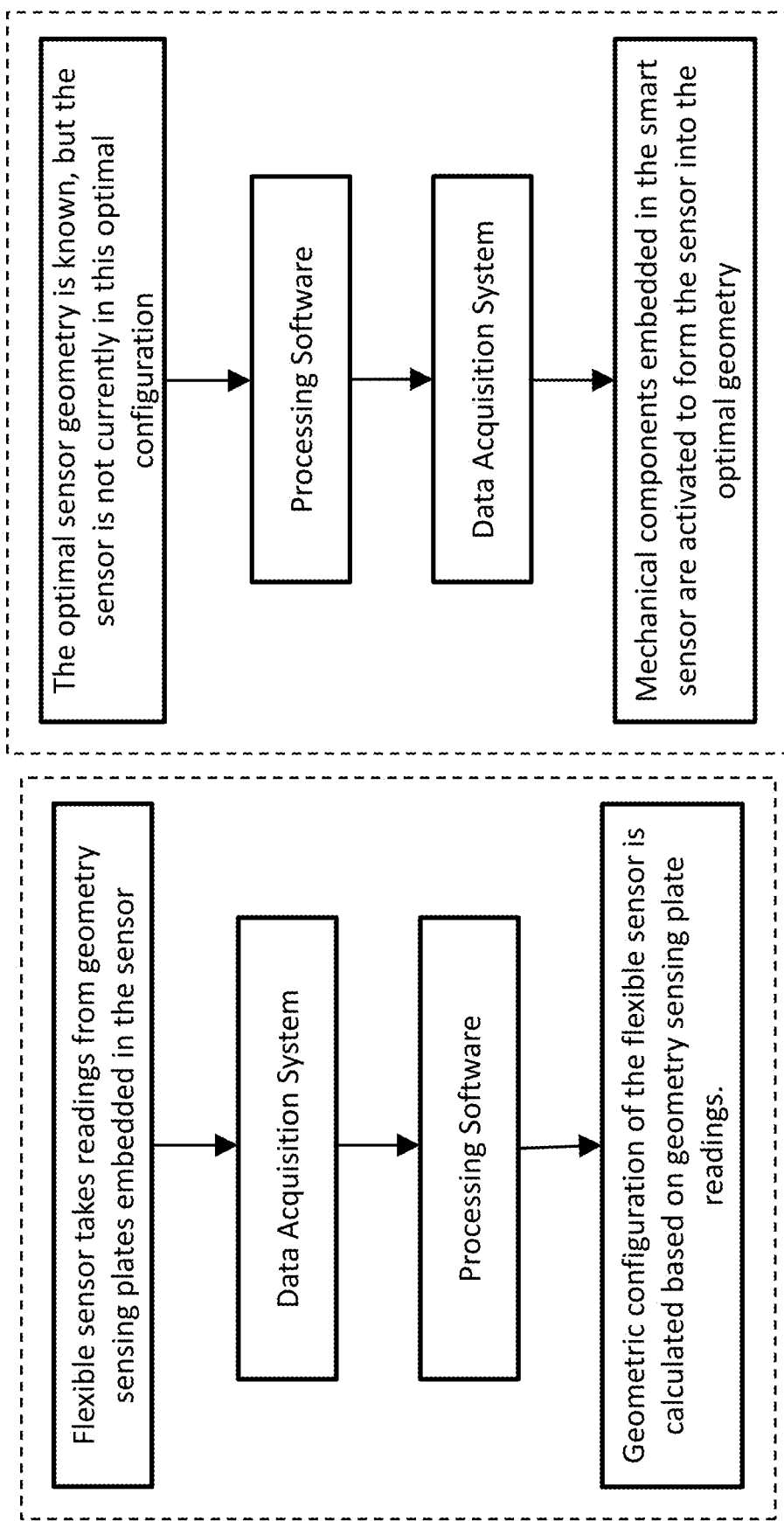
FIG. 7a illustrates one embodiment of estimating new system parameters as in FIG. 5a as the physical configuration of a smart sensor can be detected by the system to use as an additional dimension in the Multi-Dimensional Approach.
FIG. 7b illustrates one embodiment of estimating new system parameters as in FIG. 5a as the physical configuration of a smart sensor can be formed by the system to adapt to a known parameter to optimize the Multi-Dimensional Approach.

FIG. 7a illustrates an exemplary embodiment of the component of stage 1 in FIGS. 5a and 6a which deals with estimating new system parameters from measurements obtained from the sensor. In this embodiment, the new system parameter is the geometry of the smart sensor which can change and adapt its physical configuration. By detecting the shape through geometry sensing plates, the new parameter of the sensor geometry is known and can be fed back to the step which determines which dimensions to employ in measurement for optimal data collection.

FIG. 7b illustrates an exemplary embodiment of the component of stage 1 in FIGS. 5a and 6a which deals with estimating new system parameters from measurements obtained from the sensor. In this embodiment, known parameters indicate that a particular sensor geometry should be employed in data collection and mechanical mechanisms embedded in the sensor are activated to conform the sensor shape to this new geometrical configuration. This new configuration is a new parameter that can be fed back into the step which determines which dimensions to employ in measurement for optimal data collection.

FIG. 8a illustrates an exemplary embodiment of the component of stage 1 in FIGS. 5a and 6a which deals with estimating new system parameters from measurements obtained from the sensor. In this embodiment, the new system parameters are frequency transition points at which other parameters change when excited at frequencies above and below. A frequency sweep can be carried out on any parameter. These transition points are a new parameter that can be fed back into the step which determines which dimensions to employ in measurement for optimal data collection.

FIG. 8b illustrates an exemplary embodiment of the component of stage 1 in FIGS. 5a and 6a which deals with estimating new system parameters from measurements obtained from the sensor. In this embodiment, similar to FIG. 8a, a frequency sweep is employed to collect data for determining frequency transition points. In addition to the steps in FIG. 8a, a pattern recognition or data analysis step is employed to classify the system based on the specific frequency transition points identified. This new classification is a new parameter that can be fed back into the step which determines which dimensions to employ in measurement for optimal data collection.

Figure 9:
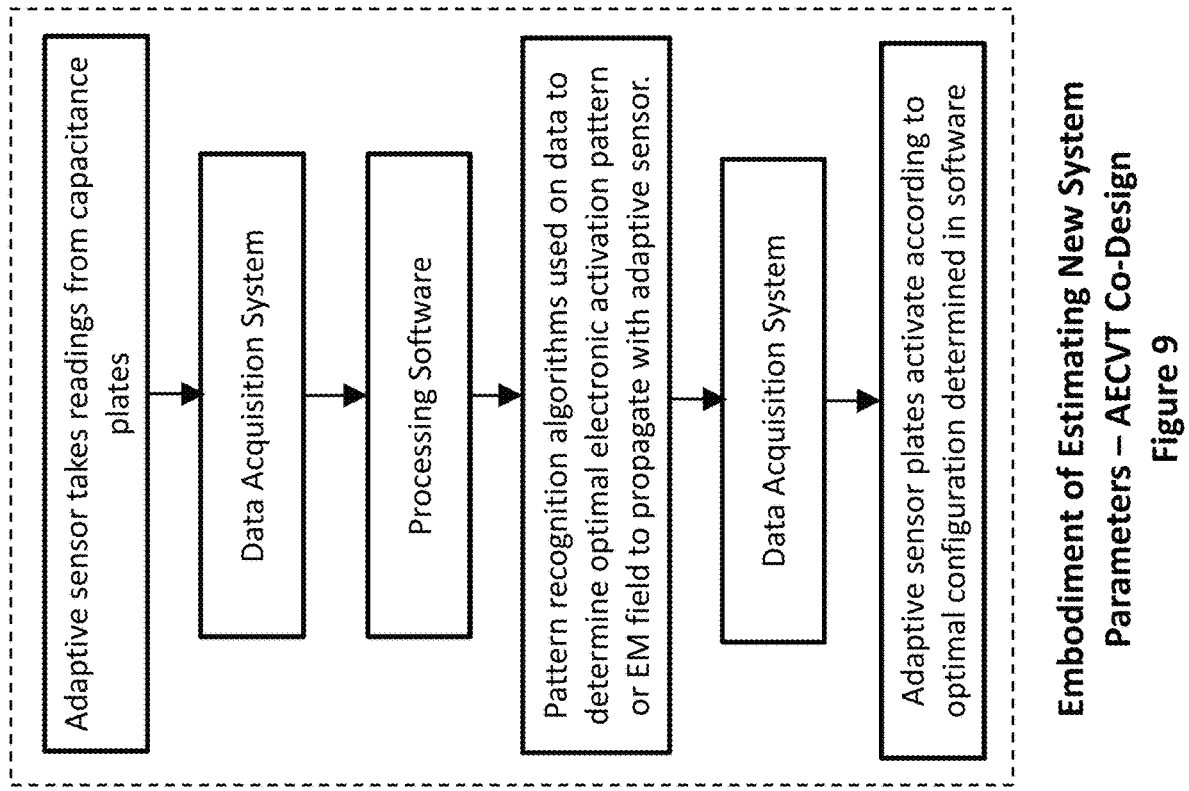
FIG. 9 illustrates one embodiment of estimating new system parameters as in FIG. 5a as AECVT is used to optimize data capture according to pattern recognition algorithms.

FIG. 9 illustrates an exemplary embodiment of the component of stage 1 in FIGS. 5a and 6a which deals with estimating new system parameters from measurements obtained from the sensor. In this embodiment, the adaptive technique for ECVT or AECVT is employed in which data is collected from an AECVT sensor and pattern recognition or data analysis helps to determine a new optimal plate activation configuration. The new optimal plate configuration is a new parameter that can be fed back into the step which determines which dimensions to employ in measurement for optimal data collection.

Figure 10:
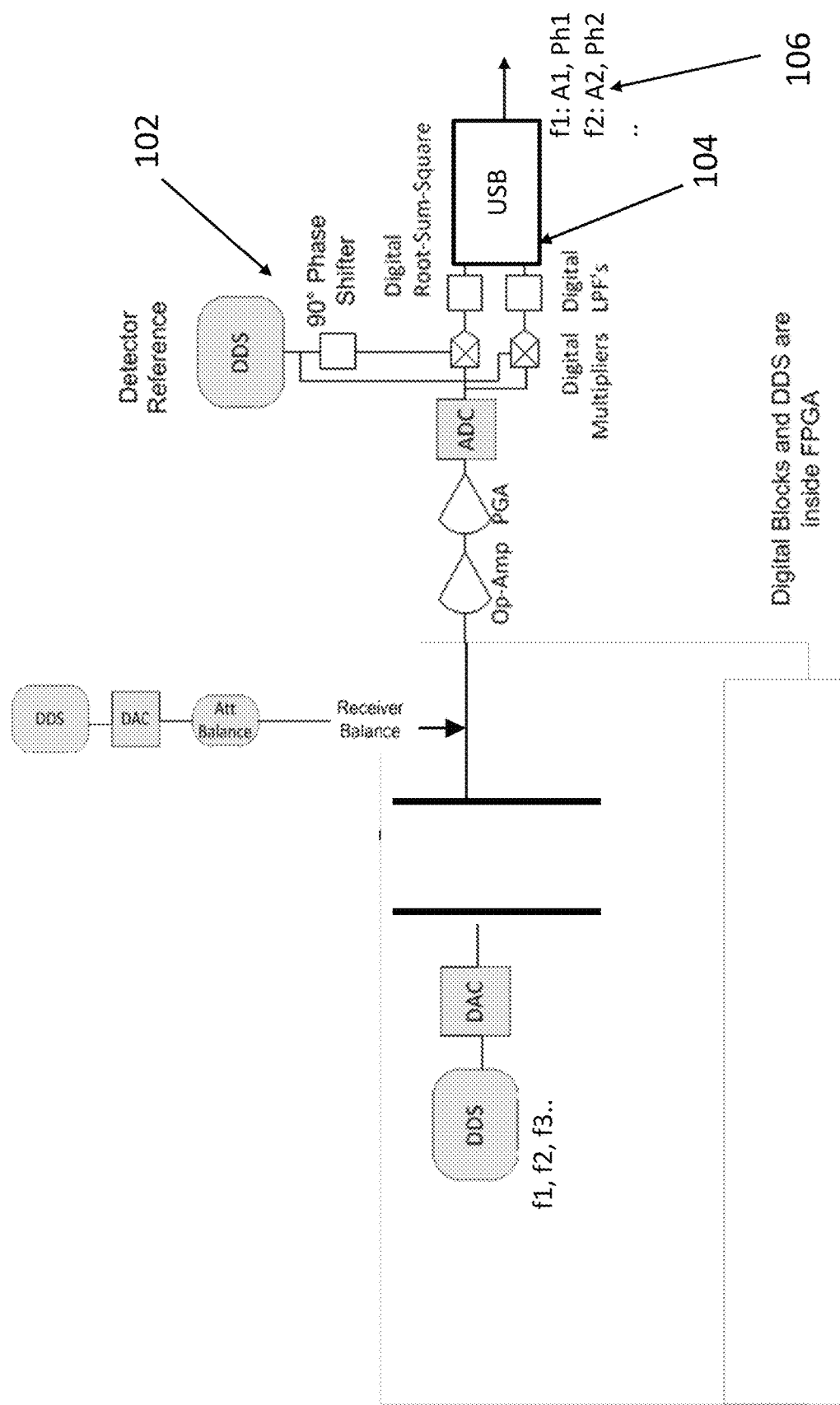
FIG. 10 illustrates one embodiment of a building block circuit for measuring receiver current amplitude and phase at different frequencies.

FIG. 10 illustrates an exemplary embodiment with single excitation and receiver channels to measure capacitance and phase of ECVT or adaptive sensor segments for single capacitance measurements. This building block can be used with other circuit components to form a full system to measure multiple capacitance values of an ECVT, AECVT, or DCPT sensor system. This building block features:

1) In-phase and quadrature parallel detectors providing two orthogonal demodulations of the received signal (104). A 90 degree phase shifter (102) provides the reference signal for the quadrature detector.

2) the amplitude and phase of the detected signal as the root mean square and arctangent of the in-phase and quadrature components, respectively (106).

3) detected signal phase to represent dielectric and lossy material properties in the multi-dimensional configuration. Amplitude and phase of the detected signal in multi-dimensional configuration are compared to amplitude and phase of a calibrated signal to decouple the material in the imaging domain from its lossy and dielectric properties. The phase is used also in the DCPT mode. Both amplitude and phase are measured at different frequencies to increase available measurement dimensions for the Multi-dimensional approach.

While certain embodiments of the present invention are described in detail above, the scope of the invention is not to be considered limited by such disclosure, and modifications are possible without departing from the spirit of the invention as evidenced by the following claims:

What is claimed is:

1. A system for generating a three-dimensional tomograph of a vessel interior or other object and for multi-phase flow decomposition, the system comprising:
   a capacitance sensor device comprising a plurality of electrodes for placement around the vessel or the object;
   an electrical circuit in communication with the capacitance sensor device for receiving input data from the capacitance sensor device, the electrical circuit adapted to output capacitance signals and electric phase signals at different frequencies;
   a hardware processing system in communication with the electrical circuit, the hardware processing system programmed with instructions for executing on the hardware processing system to: use the capacitance and electric phase signals at different frequencies to measure a volume fraction of each phase of the flow and for using each capacitance and electrical phase signal to calculate the velocity for each phase of the flow.

2. The system according to claim 1, wherein the capacitance sensor device is comprised of at least two planes of electrodes to provide sensor sensitivity in the axial and radial directions.

3. The system for generating a three-dimensional tomograph of a vessel interior or other object and for multi-phase flow decomposition according to claim 1, wherein the hardware processing system is programmed with instructions for using the product of a velocity and the volume fraction for each phase of the flow to determine mass flow rate.

4. The system according to claim 3, wherein the hardware processing system is programmed with instructions for providing real-time imaging of multiphase flow within the vessel.

5. The system according to claim 3, wherein the hardware processing system is programmed to use the volume fraction of each phase of the flow to produce a phase distribution image.

6. The system according to claim 3, wherein the hardware processing system is programmed with instructions for executing on the hardware processing system to reconstruct a three-dimensional volume-image of moving flows and stationary objects by analyzing the electric phase change of current from the capacitance sensor device.

7. The system according to claim 1, wherein the hardware processing system is programmed with instructions for executing on the processing system to measure velocity of flows that do not undergo changes in effective dielectric constant.

8. The system of claim 1, wherein each phase of the flow refers to the phase of the matter in the flow.

9. The system according to claim 1, wherein a sensitivity matrix is generated for the system by recording changes in phase with respect to changes in electric properties of flow materials.

10. The system according to claim 1, wherein the electrical circuit is further comprised of a synchronous demodulation circuit adapted to track phase changes in the current.

11. The system according to claim 9, wherein the hardware processing system is programmed with instructions for executing on the hardware processing system to use a gradient of phase sensitivity matrix to generate a three-dimensional (3D) velocity map based on phase measurements.

12. The system according to claim 1, wherein the capacitance sensor device is adapted to be operated at multiple frequencies simultaneously for probing material in the capacitance sensor device using differences in phases from various activation frequencies.

13. The system of claim 1, wherein the system is adapted to control the sensitivity of the capacitance sensor device by changing the frequency of the voltage distribution applied to at least one electrode.

14. The system of claim 1, wherein the electrical circuit is further comprised of:
- a current to voltage converter for receiving current output from the capacitance sensor device;
- a gain amplifier in electrical communication with the current to voltage converter;
- an analog to digital converter in electrical communication with the gain amplifier;
- a synchronous demodulation circuit in electrical communication with the analog to digital converter.

15. The system of claim 1, wherein the synchronous demodulation circuit is further comprised of low pass filters to filter out high frequency components of a signal received at an input to the synchronous demodulation circuit.

16. The system of claim 1, wherein the capacitance sensor device is adapted to be moved over a stationary object at a predetermined velocity and wherein the system is adapted to determine phase changes in the current.

17. The system of claim 16, wherein the hardware processing system is programmed with instructions for executing on the hardware processing system to reconstruct a three-dimensional volume-image from the phase changes.

18. The system of claim 1, wherein the hardware processing system is programmed with instructions for executing on the hardware processing system to convert the phase data to volume fraction occupied by material in the capacitance sensor device.

19. The system of claim 1, wherein the hardware processing system is programmed with instructions for executing on the hardware processing system to generate a three-dimensional (3D) velocity map by using the difference between two different phase measurements at two different times with a gradient sensitivity matrix.

20. The system of claim 1, wherein the hardware processing system is programmed with instructions for executing on the hardware processing system to reconstruct a three-dimensional volume-image from the capacitance signals at the different frequencies.

21. A system for generating a three-dimensional tomograph of a vessel interior or other object and for multi-phase flow decomposition, the system comprising:
- a capacitance sensor device comprising a plurality of electrodes for placement around the vessel or the object;
- an electrical circuit in communication with the capacitance sensor device for receiving input data from the capacitance sensor device, the electrical circuit adapted to output capacitance signals and electric phase signals at different frequencies;
- a hardware processing system in communication with the electrical circuit, the hardware processing system programmed with instructions for executing on the hardware processing system: to use the capacitance and electric phase signals at different frequencies to reconstruct a three-dimensional volume-image from the capacitance signals at the different frequencies and to use the electric phase signals at different frequencies to measure a volume fraction of each phase of the flow and for using each electrical phase signal to calculate the velocity for each phase of the flow.

22. The system according to claim 21, wherein the capacitance sensor device is comprised of at least two planes of electrodes to provide sensor sensitivity in the axial and radial directions.

23. The system for generating a three-dimensional tomograph of a vessel interior or other object and for multi-phase flow decomposition according to claim 21, wherein the hardware processing system is programmed with instructions for using the product of a velocity and the volume fraction for each phase of the flow to determine mass flow rate.

24. The system according to claim 23, wherein the hardware processing system is programmed with instructions for providing real-time imaging of multiphase flow within the vessel.

25. The system according to claim 23, wherein the hardware processing system is programmed with instructions for executing on the hardware processing system to reconstruct a three-dimensional volume-image of moving flows and stationary objects by analyzing the electric phase change of current from the capacitance sensor device.

26. The system according to claim 21, wherein the hardware processing system is programmed with instructions for executing on the processing system to measure velocity of flows that do not undergo changes in effective dielectric constant.

27. The system of claim 21, wherein each phase of the flow refers to the phase of the matter in the flow.

28. The system of claim 21, wherein the hardware processing system is programmed with instructions for executing on the hardware processing system to use the volume fraction of each phase of the flow to produce a phase distribution image.

29. A system for generating a three-dimensional tomograph of a vessel interior or other object and for multi-phase flow decomposition, the system comprising:
- a capacitance sensor device comprising a plurality of electrodes for placement around the vessel or the object;
- an electrical circuit in communication with the capacitance sensor device for receiving input data from the capacitance sensor device, the electrical circuit adapted to output capacitance signals and electric phase signals at different frequencies; and
- a hardware processing system in communication with the electrical circuit, the hardware processing system programmed with instructions for executing on the hardware processing system to: use the capacitance and electric phase signals at different frequencies to measure a volume fraction of each phase of the flow and for using the volume fraction of each phase of the flow to produce a phase distribution image.

30. The system of claim 29, wherein the hardware processing system is programmed with instructions for executing on the hardware processing system to reconstruct a three-dimensional volume-image from the capacitance signals at different frequencies and the phase changes at different frequencies.

31. The system of claim 29, wherein the hardware processing system is programmed with instructions for using a product of a velocity and the volume fraction for each phase of the flow to determine mass flow rate.

32. They system of claim 29, wherein the electrical circuit is further comprised of:
- a current to voltage converter for receiving current output from the capacitance sensor device;
- a gain amplifier in electrical communication with the current to voltage converter;
- an analog to digital converter in electrical communication with the gain amplifier;
- a synchronous demodulation circuit in electrical communication with the analog to digital converter, the synchronous demodulation circuit adapted to track phase changes in the current at different frequencies.

33. The system of claim 29, wherein volume fraction is a quantification of a volume of a first matter in relation to the total volume of all matter.

\* \* \* \* \*